(12) United States Patent
Frankel

(10) Patent No.: US 7,289,203 B2
(45) Date of Patent: Oct. 30, 2007

(54) METHOD AND SYSTEM FOR SPECTRAL ANALYSIS OF BIOLOGICAL MATERIALS USING STIMULATED CARS

(75) Inventor: Robert Frankel, Rochester, NY (US)

(73) Assignee: Chromaplex, Inc., West Henrietta, NY (US)

( * ) Notice: Subject to any disclaimer, the term of this patent is extended or adjusted under 35 U.S.C. 154(b) by 324 days.

(21) Appl. No.: 10/957,162

(22) Filed: Sep. 30, 2004

(65) Prior Publication Data

US 2006/0066848 A1   Mar. 30, 2006

(51) Int. Cl.
*G01J 3/44* (2006.01)
(52) U.S. Cl. ....................................... 356/301
(58) Field of Classification Search ............ None
See application file for complete search history.

(56) References Cited

U.S. PATENT DOCUMENTS

| | | | | |
|---|---|---|---|---|
| 4,486,884 | A * | 12/1984 | White ........................... | 372/3 |
| 4,619,528 | A * | 10/1986 | Genack et al. ............... | 356/301 |
| 2003/0007145 | A1* | 1/2003 | Shimada ...................... | 356/301 |
| 2004/0145735 | A1* | 7/2004 | Silberberg et al. .......... | 356/301 |

OTHER PUBLICATIONS

Mirkin, Chad A. "Nanoparticles with Raman Spectroscopic Fingerprints For DNA and RNA Detection", Northwestern Univ., 10th Foresight Conference, Abstract, 2 pgs, Aug. 26, 2004.

Scully, M.O., "Fast Cars: Engineering a laser spectroscopic technique for rapid identification of bacterial spores" PNAS, vol. 99, No. 17, pp. 10994-11001, Aug. 20, 2002.
dePaula, J.C., "Raman Spectroscopy of Metalloporphyrins", Chemistry 302, pp. 1-14, (downloaded Jun. 3, 2003).
Cao, YunWei Charles, "Nanoparticles with Raman Spectroscopic Fingerprints for DNA and RNA Detection", Science, vol. 297, pp. 1536-1540, Aug. 30, 2002.
Boas, Gary, "Colloidal particles improve surface-enhanced Raman scattering", PioPhotonics International, pp. 65-67, Jan. 2004.
Dudovich, Nirit, "Single-pulse coherent anti-Stokes Raman spectroscopy in the fingerprint spectral region" Journal of Chemical Physics, vol. 118, No. 20, pp. 9208-9215, May 22, 2003.

(Continued)

*Primary Examiner*—Gregory J Toatley, Jr.
*Assistant Examiner*—Gordon J. Stock, Jr.
(74) *Attorney, Agent, or Firm*—Nixon Peabody LLP

(57) ABSTRACT

A CARS system and method for probing a Raman signature of a sample are described. A short femtosecond pulse from one or more lasers is split into two pulses, a stimulus pulse and a probe pulse, whereby the probe pulse is time-delayed with respect to the stimulus pulse. Both pulses can be phase- and polarization-modulated. The stimulus pulse excites a vibronic level in the sample and the probe pulse probes molecular Raman transitions in the sample. A difference in the signals with and without excitation can be used to determine on which molecule a bond is most likely located. This will allow an accurate and sensitive determination of the presence of specific molecules in the sample. The system and method can be used to analyze biological samples and to discriminate between molecules having overlapping Raman signatures.

25 Claims, 8 Drawing Sheets

OTHER PUBLICATIONS

Oron, Dan, Femtosecond Phase-and-Polarization Control for Background-Free Coherent Anti-Stokes Raman Spectroscopy, Physical Review Letter, vol. 90, No. 21, pp. 213902-1-213902-4, May 30, 2003.

Dudovich, Nirit, "Coherent Transient Enhancement of Optically Induced Resonant Transitions", Physical Review Letter, vol. 88, No. 12, pp. 123004-1-123004-4, Mar. 25, 2002.

Oron, Dan, "Single-Pulse Phase-Contrast Nonlinear Raman Spectroscopy", Physical Review Letter, vol. 89, No. 27, pp. 273001-1-273001-4, Dec. 30, 2002.

Wright et al., "Quantitative Modeling of Nonlinear Processes in Coherent Two-Dimensional Vibrational Spectroscopy", J. Phys. Chem, A, 107:8166-8176 (2003).

* cited by examiner

METHOD AND SYSTEM FOR SPECTRAL ANALYSIS OF BIOLOGICAL MATERIALS USING STIMULATED CARS

FIELD OF INVENTION

This invention relates to the field of laser spectroscopy and more particularly to the field of Coherent Anti-Stokes Raman Spectroscopy (CARS) to identify or image the presence of specific organic molecules.

BACKGROUND TO THE INVENTION

Raman spectroscopy and Raman microscopy are conventionally used to measure the vibration levels of molecules in solution, in the gas phase, solid phase or on surfaces. In a Raman scattering process, a molecule can absorb energy from an incident photon, with scattered photons being down-shifted in energy (Stokes shift). Scattered photons can also gain energy from populated vibronic states of the molecule and are up-shifted in energy (Anti-Stokes shift). The ensemble of Stokes-shifted lines are referred to as vibronic molecular fingerprint of the molecule.

Disadvantageously, in conventional Raman spectroscopy, fluorescent emission can coincide with the Stokes-shifted Raman spectrum to be measured. Short laser pulses and time-gated signal detection may be employed to alleviate the adverse effects caused by fluorescence. Spectra of complex organic molecules in mixtures may also overlap, making it difficult to determine an association between the measured spectra and the molecules of interest. The low efficiency of scattering <$10^{-6}$ for non-resonant scattering, and background scattering may also require concentrations of molecules of interest in excess of 1% of scattering molecules which may be impractical.

Coherent Anti-Stokes Raman Spectroscopy (CARS) has recently been used to address many of the aforementioned problems. As illustrated in FIG. 1, CARS is a four-wave mixing process using three photons ($\omega_{p1}$, $\omega_s$, $\omega_{p2}$) to prepare a vibronic or rotational state, stimulating the resulting in the emission of a fourth photon ($\omega_3$) that is blue-shifted relative to the other three photons. The first photon ($\omega_{p1}$) is called the pump photon, while the second photon ($\omega_s$) is called the Stokes photon. The third photon ($\omega_{p2}$), the probe photon, drives the electron to a virtual level from which the fourth photon ($\omega_3$) is emitted as the electron returns to the ground state. Since vibronic excited states relax on a picosecond to sub-picosecond time scale, the process is most efficient when activated by sub-picosecond laser pulses. The signal strength is greatly enhanced over conventional Raman spectroscopy because the CARS process is a stimulated process and increases as the square of the laser intensity.

It has recently been reported by Oron et al. (*Physical Review Letters* Vol. 90, No. 21, pp. 213902-1 to -4 (2003)) that all three stimulating CARS photons ($\omega_{p1}$, $\omega_s$, $\omega_{p2}$) can be supplied by a single laser pulse and that an incoherent CARS background can be substantially reduced by controlling the laser polarization and the phase of arrival of the photons from the pulse at the molecule.

FIG. 2 shows a conventional single laser setup 20 for CARS spectroscopy which includes a phase and polarization controller 24. A laser 22, for example, a Ti: Sapphire laser, generates a femtosecond laser pulse. The laser pulse then passes through a spectral phase/pulse shaper 24 which can include, for example, a liquid crystal spectral light modulator (SLM) 244 and two gratings 242 and 246 that spectrally disperse and recombine/compress the pulse for laser 22. Pulse shaper 24 can also control the phase and polarization of the laser radiation emitted by laser 22. The shaped pulse exiting the spectral phase/pulse shaper 24 is then focused onto the sample 25, and the CARS signal is measured, for example, with a dispersive spectrometer 26 or a monochromator 26 with a photodetector, such as a photomultiplier tube, and analyzed in spectral analyzer 27. The phase/polarization controller 24 can be controlled by, for example, the spectral analyzer 27 via a data and control line 28. Although detection of the CARS signal is shown in transmission, a back scattered signal can also be detected.

However, the conventional CARS spectroscopy may not be able to associate, for example, in complex mixtures of molecules, the various Raman lines with the fingerprint of specific constituent molecules. This molecular spectral dissection is presently accomplished with chemometric spectral analysis algorithms that applies mathematical and statistical techniques to the analysis of complex data. However, this approach tends to be limited to less than ten overlapping fingerprints and may require concentrations of the constituent molecules of greater than 1% in solutes.

It would therefore be desirable to overcome the shortcomings of the conventional Raman measurement techniques and analytical methods, which would allow a spectroscopic analysis of complex mixtures of organic molecules and an unambiguous determination of the constituents.

SUMMARY OF THE INVENTION

The systems and methods described herein use single laser Coherent Anti-Stokes Raman Spectroscopy (CARS), more particularly with quantum phase control, to determine the molecular fingerprints of multiple analytes in a solution or in the image field of a microscope. More particularly, the systems and methods employ vibronic state population preparation in conjunction with single laser CARS.

According to one aspect of the invention, a CARS system for probing a Raman signature of a sample includes one or more laser, that can be synchronized, for example, by mode-locking, emitting a femtosecond laser pulse, a beam splitter that splits the laser pulse into a stimulus pulse and a probe pulse, a first spectral phase modulator modulating a phase and/or a polarization of the stimulus pulse, a second spectral phase modulator modulating a phase and/or polarization of the probe pulse, an optical delay line for time-delaying the modulated probe pulse with respect to the stimulus pulse, and a spectral analyzer that detects the Raman signature of the sample in response to the probe pulse and after stimulation of the sample by the stimulus pulse.

According to another aspect of the invention, a method for identifying molecules in a molecular system based on a stimulated CARS signature includes the steps of providing a first optical probe pulse and measuring a first CARS response signal from the molecular system, providing an optical stimulus pulse and a second optical probe pulse that is time-delayed with respect to the stimulus pulse, measuring with the second optical probe pulse a second CARS response signal from the molecular system, and subtracting the first CARS response signal from the second CARS response signal to form a difference signal. The above steps are then repeated with a different optical stimulus pulse that excites a different vibronic state in the molecular system, and the molecules and a concentration of the molecules in the molecular system are identified based on the difference signal.

Embodiments of the invention may include one or more of the following features. The optical delay line may be a free-space delay line and provide a variable time delay between the stimulus pulse and the probe pulse at the sample. The laser may be a semiconductor laser or a Ti:Sapphire laser or another laser capable of producing femtosecond pulses. One or both phase modulators may include a liquid crystal to provide phase and/or polarization adjustment, as well as a pulse stretcher and/or pulse compressor implemented, for example, with a grating.

The spectral analyzer advantageously detects Raman signatures of the sample in response to the probe pulse both with and without stimulation of the sample by the stimulus pulse and computes a difference between the Raman signatures detected with and without stimulation. A non-zero difference signal indicates a CARS signal from a molecular bond of a molecule that is different from a molecular bond stimulated by the stimulus pulse.

According to another advantageous embodiment, the Raman-active molecules can be attached to nanoparticles to provide Raman tags which enhance the CARS response signal. The Raman tags can bond to biological materials to be probed, thus facilitation analysis of the bond structure of complex biological materials by molecular fingerprinting.

Further features and advantages of the present invention will be apparent from the following description of preferred embodiments and from the claims.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF EXEMPLARY EMBODIMENTS

Figure 3A:
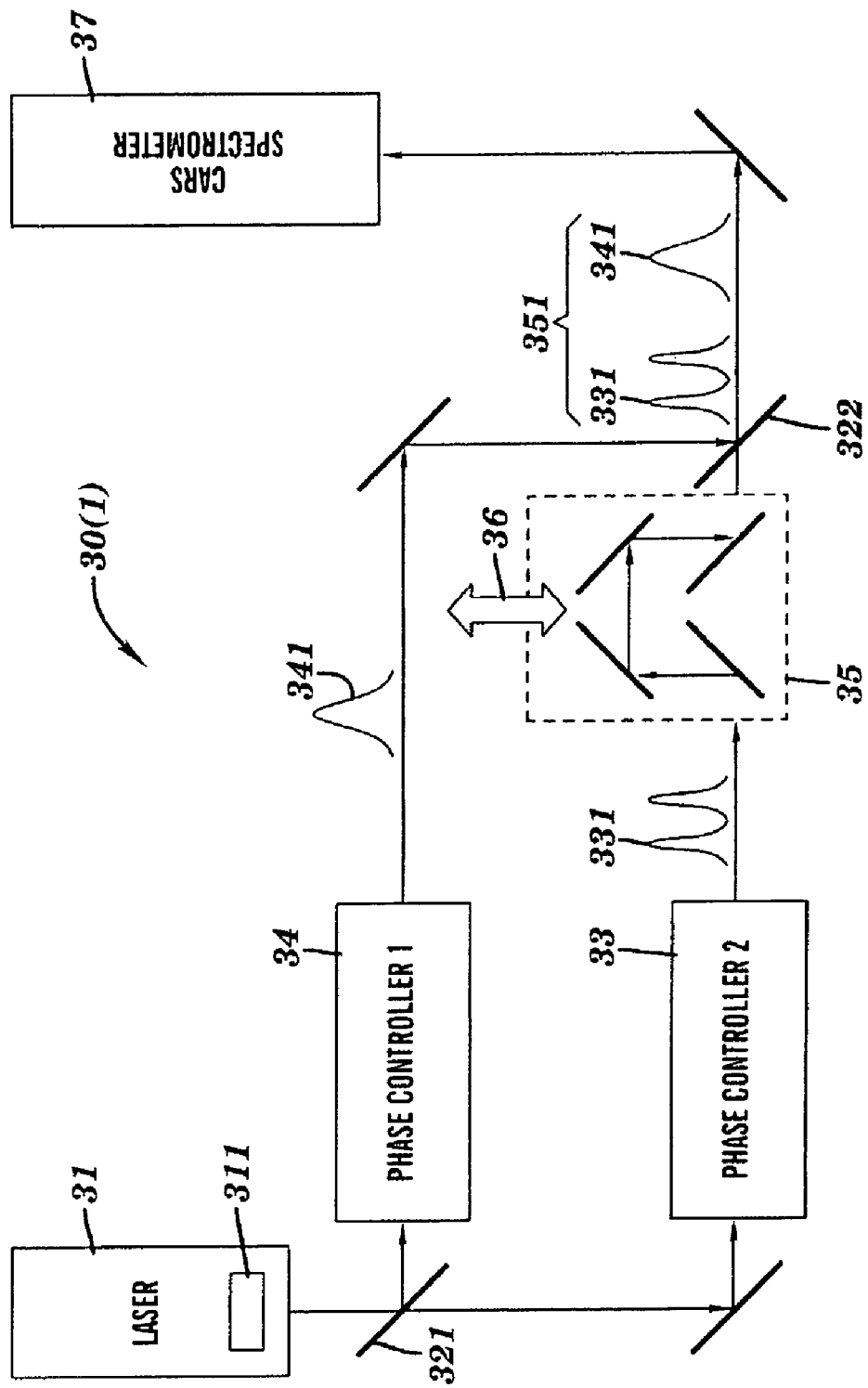
FIG. 3A shows a single laser CARS system according to embodiments of the invention.
Figure 3B:
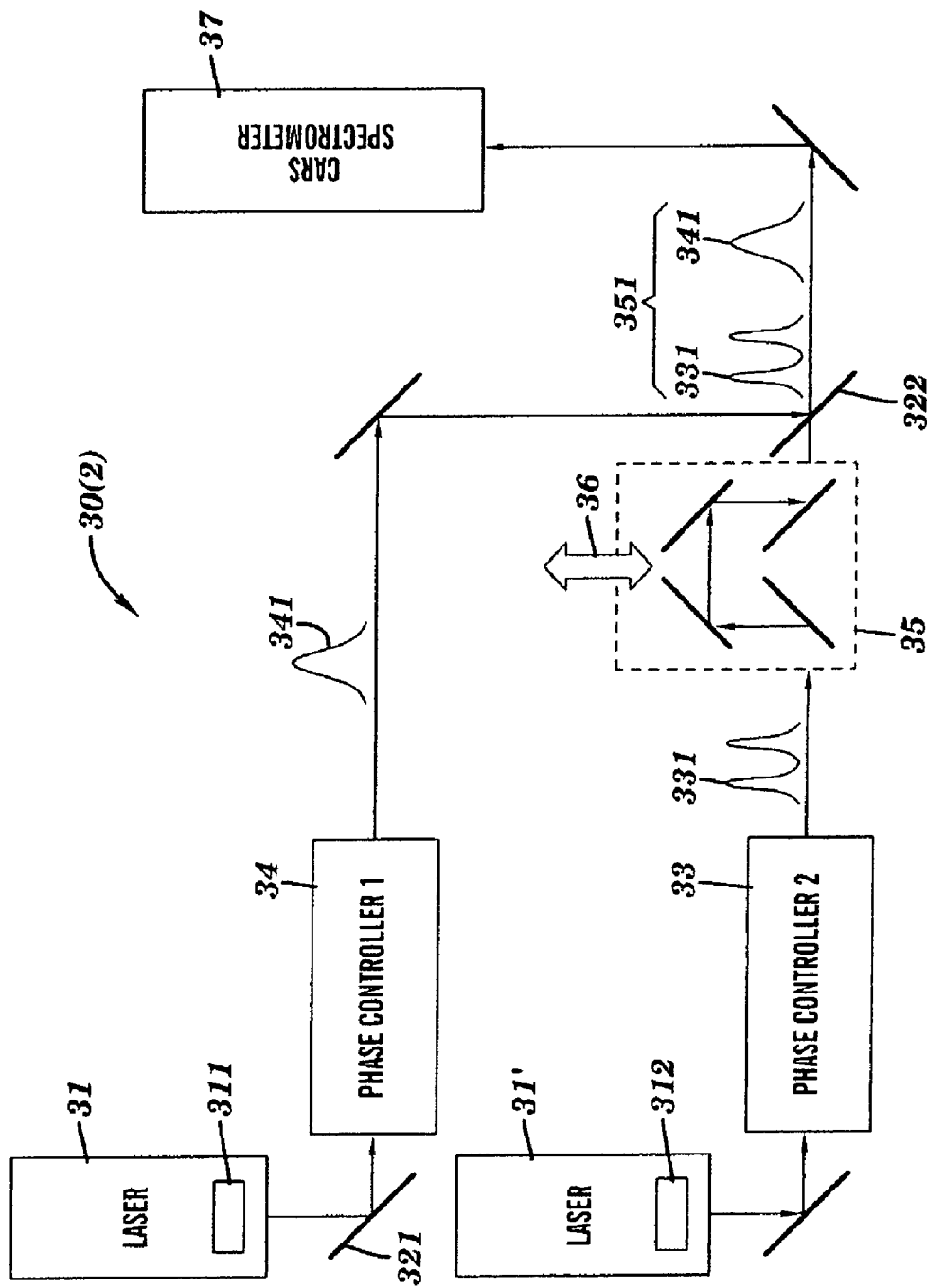
FIG. 3B shows a plurality of lasers CARS system according to other embodiments of the invention.

Referring now to FIGS. 3A and 3B, in a CARS laser system 30(1), a femtosecond or sub-picosecond laser pulse from a laser 31, preferably a mode-locked laser having a mode-locker 311, (or a plurality of lasers 31, 31' having mode-lockers 311, 312, which can be synchronized in a CARS laser system 30(2))is directed by suitable optical components, such as mirrors, prisms, etc., onto a partially reflecting mirror 321 which splits the beam into two parts. By using two or more synchronized, for example, passively or actively mode-locked, lasers 31, 31', a wider spectral range of the stimulus pulse 341 and the probe pulse 331 can be covered, as will be described below.

Figure 2:
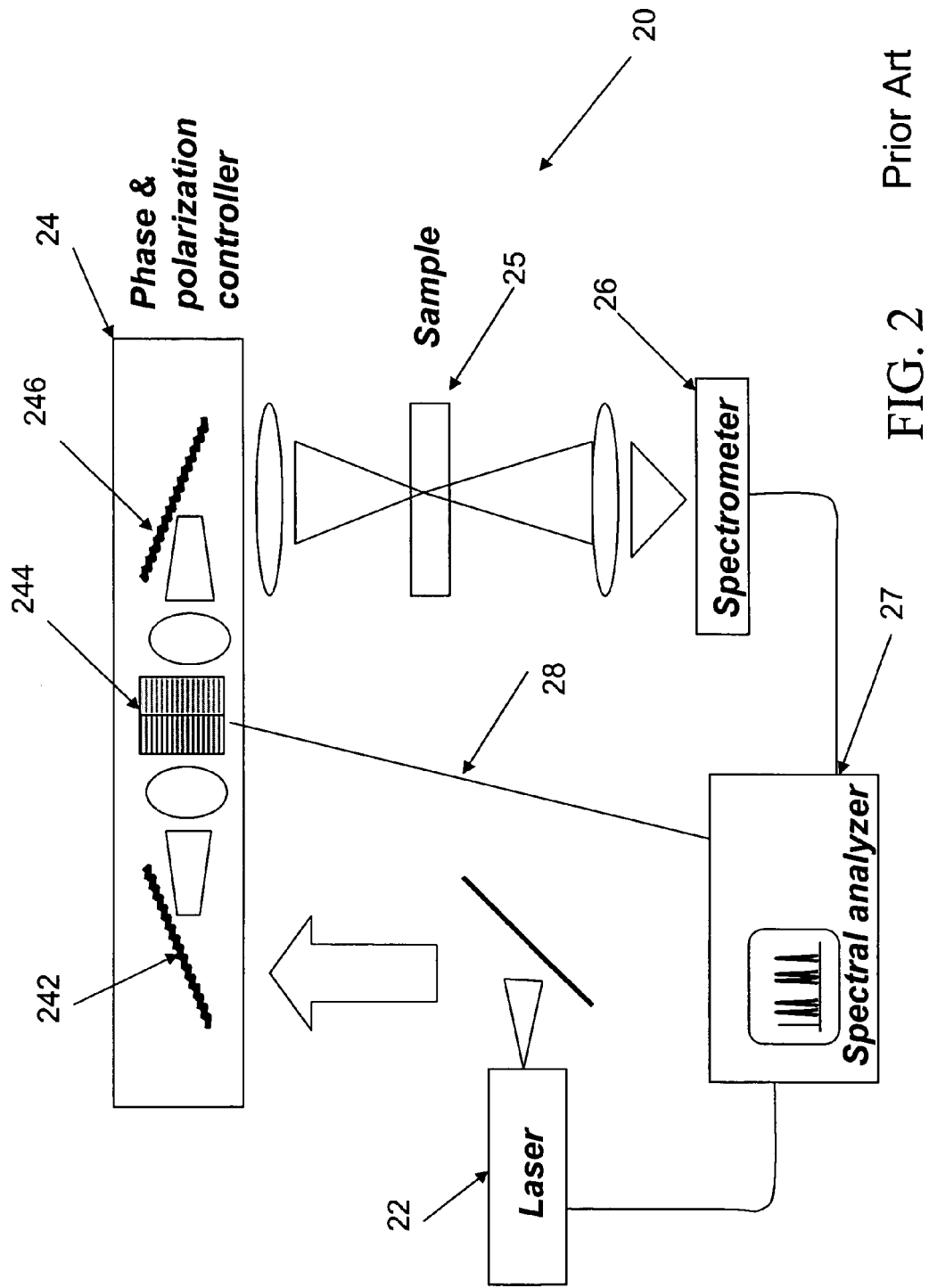
FIG. 2 shows schematically a prior art single laser CARS system.

A first part of the laser pulse is spectrally phase-modulated by a first phase/polarization controller 34, which can be implemented using optical components similar to those of phase controller 24 depicted in FIG. 2, such as a first dispersion grating, a spectral phase and polarization modulator, for example, a liquid crystal array, followed a second dispersion grating (see FIG. 2). The second part of the laser pulse passes through a second phase/polarization controller 33. This system is used to adjust the laser pulse phase and polarization to perform multiplexed CARS. The spectrally phase-modulated pulse 341 emerging from the first phase/polarization controller 34 represents a stimulus pulse that enhances the population of the excited state of a specific vibronic level in a defined molecular bond, such as the bond $V_A$ described below with reference to FIG. 6. The second spectrally phase-modulated laser pulse 331 emerging from the second phase/polarization controller 33 represents a CARS probe pulse that measures the Raman signal from the same or from a another molecular bond $V_B$ located close to the bond $V_A$ (see also FIG. 6). The probe pulse 331 passes through an optical time delay system 35, for example a free space optical delay line with an adjustable optical path length, as indicated by arrow 36. Time delays useful for characterizing bonds by CARS spectroscopy are, for example, between 10 and 1000 fs ($10^{-14}$-$10^{-12}$ sec). The delay line can be designed so as not to introduce dispersion or a change in polarization. The stimulus pulse is combined with the time-delayed pulse 331 by partially reflecting mirror 322 to form pulse train 351 consisting of the stimulus pulse 341 followed by the probe pulse 331. The combined pulse is then directed by suitable optics to a sample (not shown), similar to the arrangement shown in FIG. 2, with the response analyzed and optionally displayed in CARS spectrometer 37. The imaging optics and the CARS microscope are conventional in design and will therefore not be described. The experiment can then be conducted with or without the stimulus pulse so as to selectively identify bonds and bonding sites in molecules.

Figure 1:
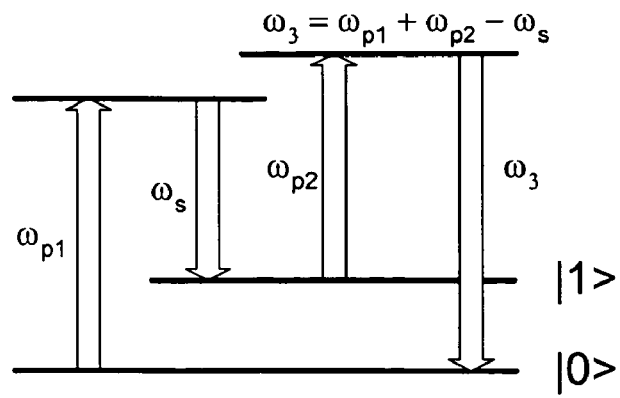
FIG. 1 shows a schematic diagram of a prior art CARS process.
Figure 4:
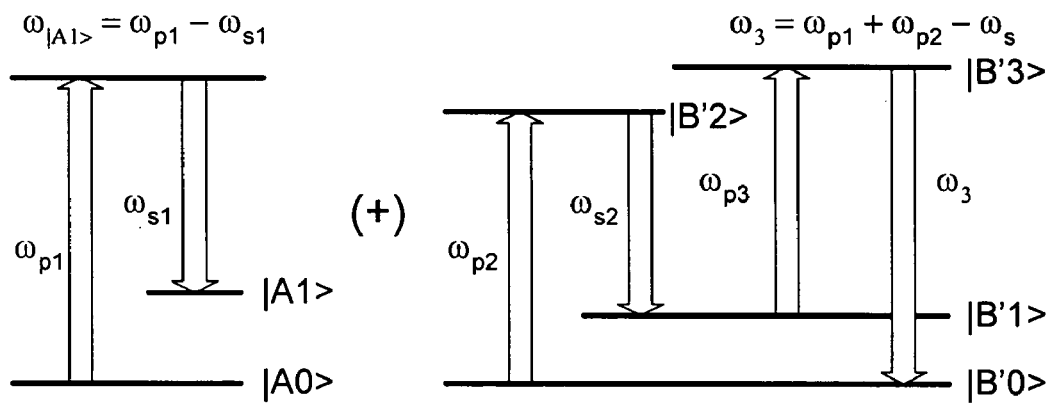
FIG. 4 shows schematically a CARS correlation process according to the invention.
Figure 4:
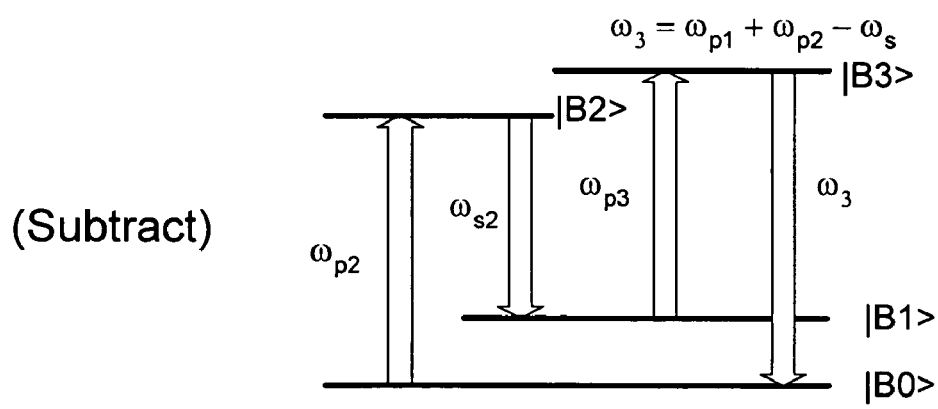
Figure 6:
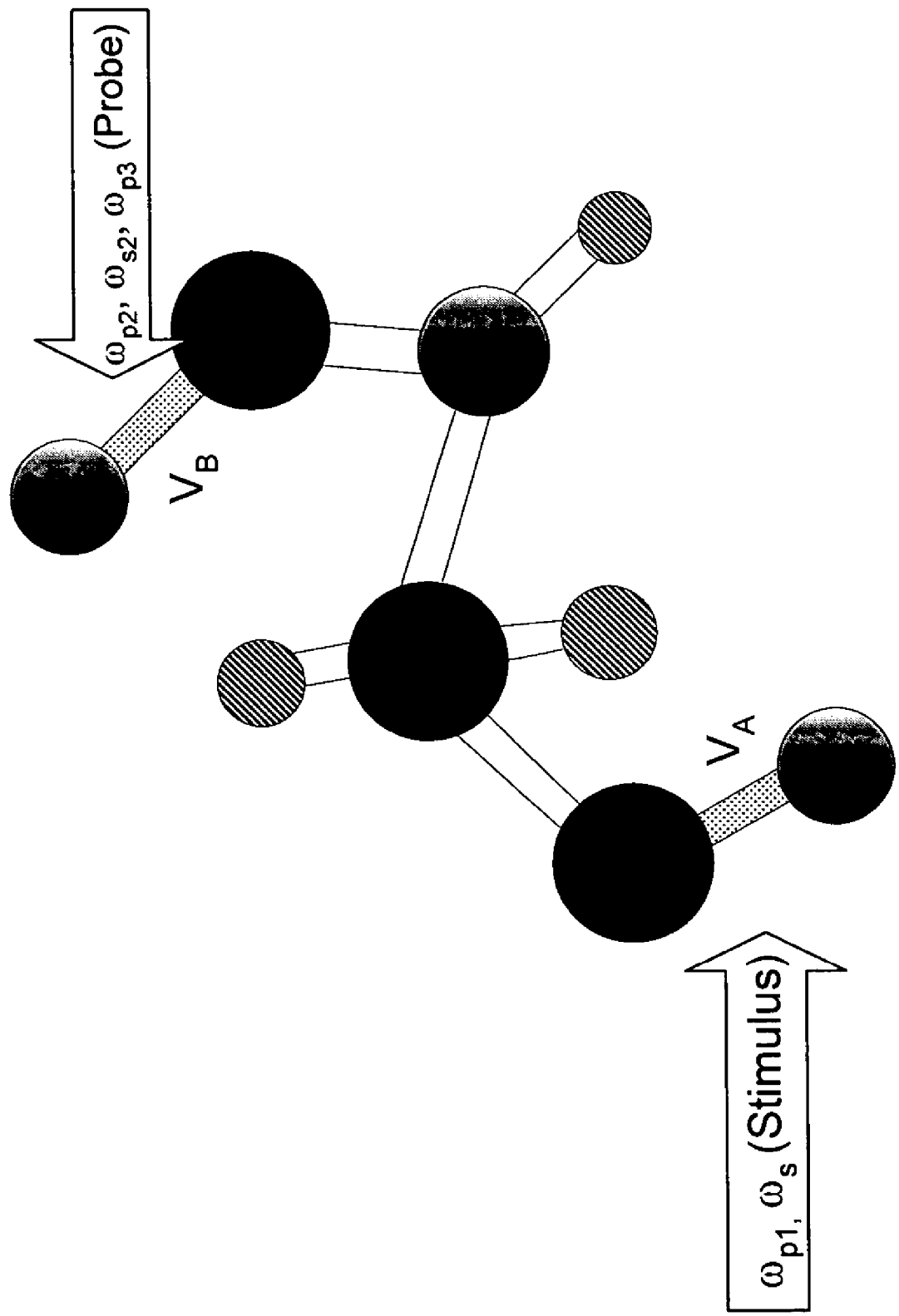
FIG. 6 shows schematically a probe pulse probing a molecule with a connected bond altered by a stimulus pulse.

Referring now to FIGS. 4 and 6, the underlying concept in the system and method according to the invention implies that an excited state electron of a particular vibronic level of the prepared (stimulated) state can alter the vibronic levels of bonds on the same molecule and also of bonds on other molecules that are in close proximity to the prepared state. Placing one or more bonds in an excited state changes the charge field distribution in the molecule and affects the energies of the other vibronic states in the excited molecule.

Referring now specifically to FIG. 4, the vibronic state of a bond $V_A$ is prepared by the stimulus pulse with a wavelength corresponding to a pump photon $\omega_{p1}$ and a Stokes photon $\omega_{s1}$, which populates energy level |A1>. The population of energy level |A1> of bond $V_A$ changes the energy of energy levels |B'0>, |B'1>, |B'2>, and |B'3> of bond $V_B$ relative to the corresponding energies |B0>, |B1>, |B2>, and |B3> when bond $V_B$ is not stimulated. The CARS spectrum is acquired by stimulating only at the vibronic energy levels of interest and measuring the response of the spectral range where a Raman response can be expected. A spectrum acquired without vibronic state preparation (stimulus) is then subtracted from the spectrum acquired with the stimulus to create a series of difference spectra or correlation spectra. The Raman frequencies where the difference spectra is non-zero, are likely to represent the response from bonds located in close proximity to the excited population, with a great likelihood that these bonds are present on the same molecule. The difference spectra can be mapped across a wide vibronic excitation space (stimulus frequencies) which can help identify the molecules, for example, molecules in solution, based on their fingerprints.

As schematically shown in FIG. 6, stimulation of bond $V^A$ by the Raman state preparation pump pulse can alter the vibronic frequency of a nearby bond $V_B$ on the same molecule or a molecule in close proximity of the stimulated molecule. Shown here is a molecule with two nearby bonds $V_A$ and $V_B$ located on the same molecule. A pump pulse of two photons $\omega_{p1}$ and is $\omega_{s1}$ used to prepare bond $V_A$ in an excited state. Then, with a delay of about 100-500 femtoseconds, a three photon ($\omega_{p2}$, $\omega_{s2}$, $\omega_{p3}$) CARS pulse is used to probe the energy level of bond $V_B$. If the bonds are connected on the same molecule or very close, it is very likely that the resonant frequency and or strength of emission of the CARS signal from $V_B$ will be altered by the preparation of $V_A$. The molecular coupling between nearby, but not directly connected dipoles scales with the inverse $6^{th}$ power of the distance between molecules which is representative of Forster energy transfer. Bonds on the same molecule may couple over larger distances via electron delocalization or charge redistribution.

Figure 5:
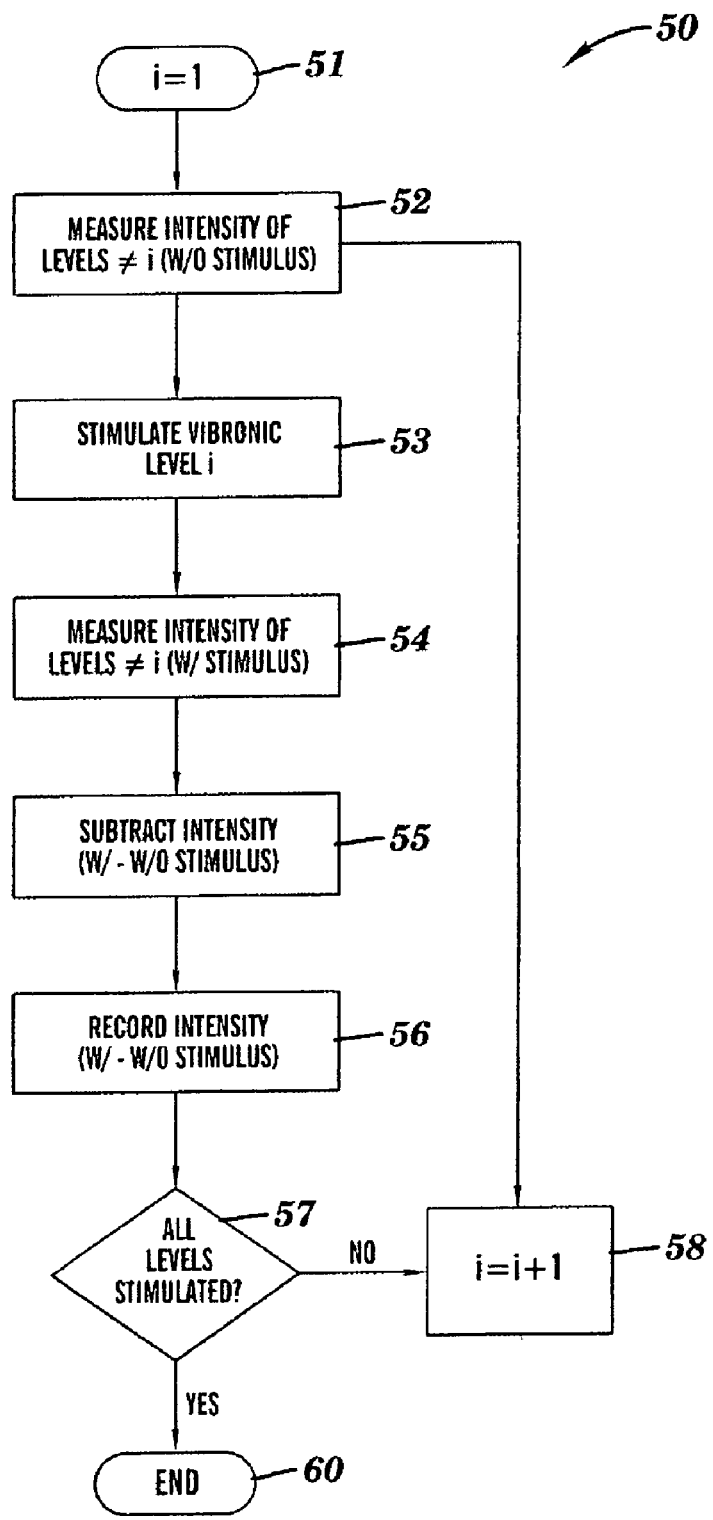
FIG. 5 shows schematically a process flow according to the invention for obtaining a molecular fingerprint with the systems of FIGS. 3A and 3B.

FIG. 5 shows a schematic process flow 50 for detecting a molecular fingerprint by single-laser stimulated CARS spectroscopy. It will be assumed that CARS spectroscopy according to the invention is performed on a molecular system with molecules having bonds $V_i$ with vibronic levels. The bonds $V_i$ can be located on the same molecule or on different molecules.

The process 50 starts at a bond $V_i$ with an arbitrarily selected vibronic energy level |A1> (see FIG. 4) with energy $\omega_i = \omega_1$ (i=1) to be stimulated, step 51. The CARS signal is then measured for all bonds $V_m$ whereby m can include the bond i, step 52. The bond energy level $\omega_1$ is then stimulated with a laser pulse having energies $\omega_{p1}$ and $\omega_{s1}$ corresponding to bond $V_A$ to "prepare" the vibronic transition on bond $V_A$, step 53. Within a time frame shorter than the relaxation time of energy level |A1> the intensity of all CARS processes with energies $\omega_m \neq \omega_i$ corresponding to the bonds $V_m \neq V_i$ is measured, step 54. The intensity difference of the measurement signals with and without stimulation is computed for all m levels, including the level $\omega_i$, step 55, and recorded, step 56. A non-zero difference in the spectral features indicates Raman-active bonds on the same molecule or on close-by molecules, step 56, since the dipole coupling strength between unconnected molecular sites, decrease with the inverse $6^{th}$ power of their spacing. Absolute intensity difference in the spectral features relative to differences of all levels indicates the number of different molecules with same pump and probe frequencies. The process 50 then repeats, steps 57, 58, going back to 52, until all vibronic levels of interest have been stimulated, as decided in decision step 57. The process 50 then terminates in step 58 with a report of the detected molecules.

As mentioned above, the stimulated CARS response is measured and recorded for all bonds $V_m$ of interest, which requires probe pulses 331 with a range of photon energies ($\omega_{p2}$, $\omega_{s2}$, $\omega_{p3}$) delivered by laser 31 and/or 31' and tuned by phase controller 33. In addition, the time interval between the stimulus pulse 341 and the probe pulse 331 can be adjusted by delay line 35.

The molecular absorption and scattering cross-sections determining the signal strength of the measured CARS signal can be enhanced by performing state preparation and CARS probing experiments with resonance excitation in the electronic absorption band of the molecules being tested. Traditionally, CARS and population inversion in vibronic levels is done through virtual intermediate levels having a low absorption cross section. The relatively long absorption length facilitates measurements with IR wavelengths and transmission through, for example, biological media and/or in vivo. Conversely, absorption by a real electronic level (instead of a virtual level) can increase the absorption efficiency by several orders of magnitude. The absorption bands of dyes are in the 400-800 nm spectral region. Small organic molecules absorb in the 210-230 nm region, while proteins, DNA and RNA absorb in the 260-300 nm region. UV excitation can be accomplished, for example, by frequency upconverting the single laser CARS pulse (e.g., frequency tripling or quadrupling in a non-linear crystal) into the UV.

Figure 7:
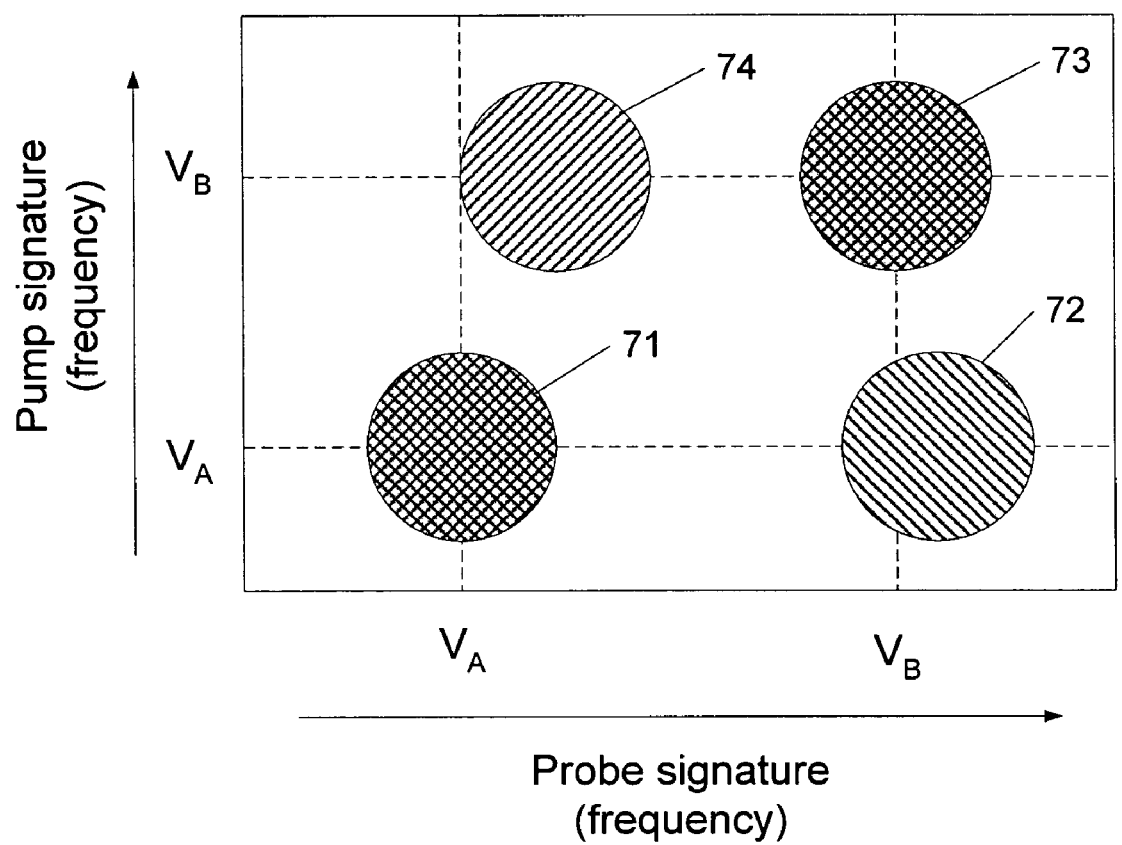
FIG. 7 shows schematically an exemplary shift in the CARS spectral response, when a connected bond is altered by a stimulus pulse.

FIG. 7 shows schematically the CARS response detected from a molecule with two connected bonds $V_A$ and $V_B$. A pump pulse of two photons is used to prepare bond $V_A$ in an excited state, as described above with reference to FIG. 4. Then, with a delay of about 100 femtosecond, a three photon CARS pulse is used to probe the energy levels of bond $V_B$. If the bonds are connected on the same molecule it is very likely that the resonant frequency and or strength of emission of the CARS signal from $V_B$ will be altered by the preparation of $V_A$, as indicated by the shift of the circle 72 off-center to the right. The signature 71 of bond $V_A$ will, of course, not move, since $\omega_{p2} = \omega_{p1}$ and $\omega_{s2} = \omega_{s1}$ in FIG. 4. A similar argument can be made for the shift of CARS signature 74 to the right, when a pump pulse is used to prepare bond $V_B$ and the CARS signal from $V_A$ is measured. Again, the CARS signature 73 of bond $V_B$ remains unchanged.

Figure 8:
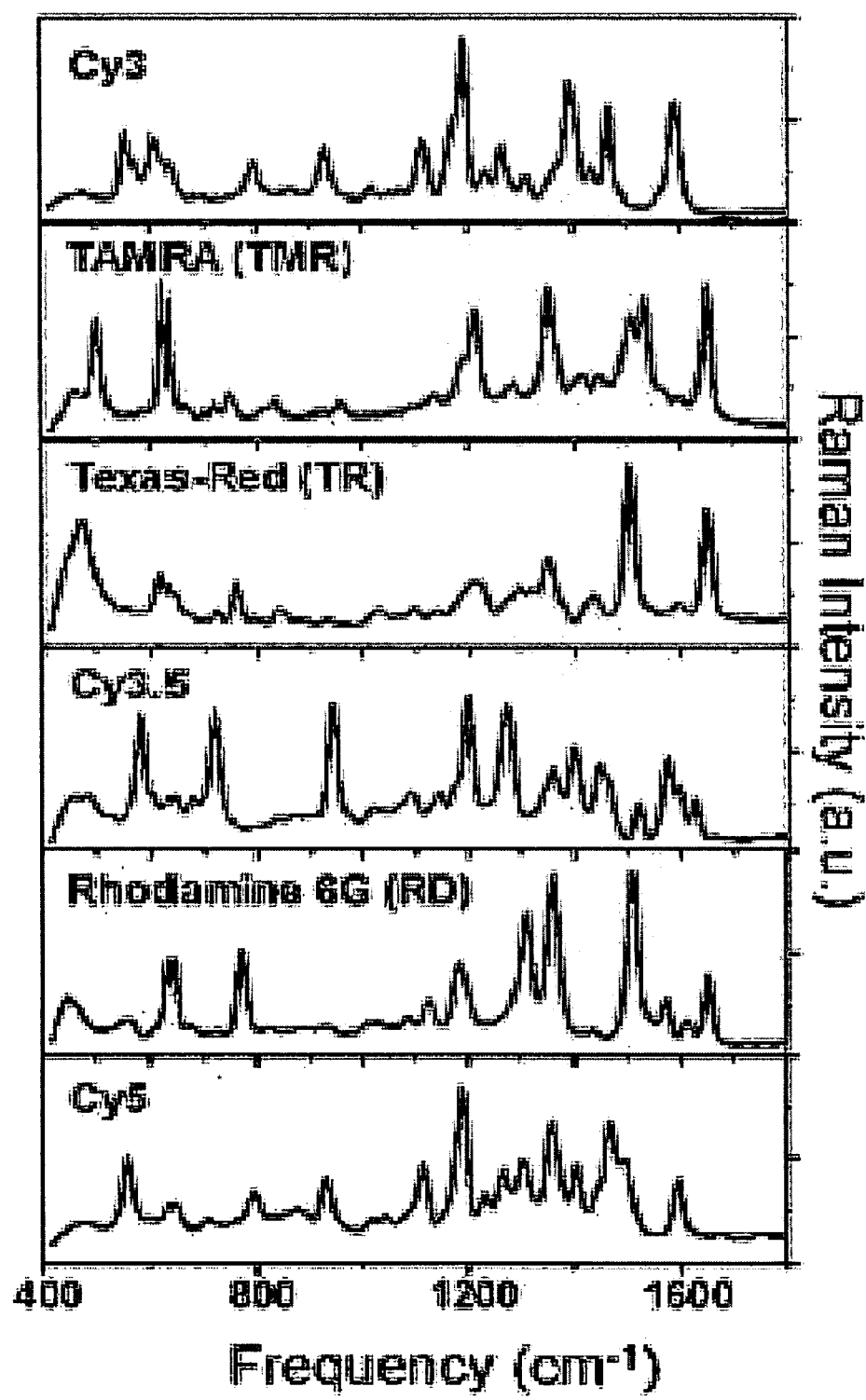
FIG. 8 shows a series of Raman spectra from conventional dyes.

FIG. 8 shows a series of Raman spectra from standard dyes useful for, for example, biochip assays These dyes may bind to proteins, DNA, RNA or nanoparticles and used to tag specific molecules in a cell. As seen in FIG. 8, many of the features in the Raman spectra of these dyes overlap in frequency. These features can be separated by stimulating the dyes with a wavelength that represents an absorption of a specific bond in the dye. The presence of specific dyes attached to, for example, biological molecules can be detected by using the stimulated CARS spectroscopy described above. The information acquired here may be used to measure the response of cells to chemotherapeutic agents, the genetic make up of cells in cancer pathologic section, or the developmental stage of a cell in an embryo.

While the invention has been disclosed in connection with the preferred embodiments shown and described in detail, various modifications and improvements thereon will become readily apparent to those skilled in the art. For example, multiple samples can be scanned and analyzed simultaneously or sequentially. A confocal microscope can provide depth resolution in the Z-direction, while the sample can move on a translation stage in the X- and Y-direction. More than one laser, for example, lasers operating as parallel sources and synchronized, e.g., mode-locked, on a femtosecond time scale may be used as a source for the stimulus and probe pulses. The time delay between the stimulus pulse and the probe pulse can be adjusted to further discriminate between spectral CARS features. Accordingly, the spirit and scope of the present invention is to be limited only by the following claims.

What is claimed is:

1. A CARS system for probing a Raman signature of a sample, comprising at least one laser producing a femtosecond laser pulse;

a beam splitter splitting the femtosecond laser pulse into a stimulus pulse and a probe pulse;

a first spectral phase modulator modulating a phase or a polarization, or both, of the stimulus pulse;

a second spectral phase modulator modulating a phase or polarization, or both, of the probe pulse;

an optical delay line for time-delaying the modulated probe pulse with respect to the stimulus pulse; and a spectral analyzer that detects the Raman signature of the sample in response to the probe pulse and after stimulation of the sample by the stimulus pulse.

2. The CARS system of claim 1, wherein the optical delay line provides a variable time delay between the stimulus pulse and the probe pulse at the sample.

3. The CARS system of claim 2, wherein the optical delay line is a free-space delay line.

4. The CARS system of claim 1, wherein the at least one laser comprises a Ti:S laser.

5. The CARS system of claim 1, wherein at least one of the phase modulators comprises a liquid crystal.

6. The CARS system of claim 1, wherein at least one of the phase modulators comprises a grating operating as a pulse stretcher.

7. The CARS system of claim 1, wherein at least one of the phase modulators comprises a grating operating as a pulse compressor.

8. The CARS system of claim 1, wherein the sample comprises at least two different types of molecules having Raman signatures.

9. The CARS system of claim 1, wherein the spectral analyzer detects Raman signatures of the sample in response to the probe pulse both with and without stimulation of the sample by the stimulus pulse and computes a difference between the Raman signatures detected with and without stimulation.

10. The CARS system of claim 1, wherein the at least one laser is a mode-locked laser.

11. The CARS system of claim 1, comprising at least two lasers providing synchronized mode-locked femtosecond laser pulses incident on the beam splitter.

12. A method comprising:

providing a molecular system;

providing a first optical probe pulse and measuring a first CARS response signal from the molecular system;

providing an optical stimulus pulse and a second optical probe pulse that is time-delayed with respect to the stimulus pulse;

measuring with the second optical probe pulse a second CARS response signal from the molecular system;

subtracting the first CARS response signal from the second CARS response signal to form a difference signal;

repeating the providing the first optical probe pulse, the providing the optical stimulus pulse, the measuring with the second optical probe pulse, and the subtracting the first CARS response signal with a different optical stimulus pulse;

providing an identification of molecules and a concentration of the molecules in the molecular system based on the difference signal; and providing an analysis of the molecular system based on the identification of the molecules and the concentration of the molecules in the molecular system.

13. The method of claim 12, wherein a non-zero difference signal indicates a CARS signal from a molecular bond of a molecule that is different from a molecular bond stimulated by the stimulus pulse.

14. The method of claim 12, wherein the optical time delay is variable.

15. The method of claim 14, wherein the optical time delay is produced by a free-space delay line.

16. The method of claim 12, wherein the first optical probe pulse, the second optical probe pulse and the stimulus pulse are produced by at least two lasers.

17. The method of claim 12, wherein the first optical probe pulse, the second optical probe pulse and the stimulus pulse are produced by a single laser.

18. The method of claim 12, wherein the second optical probe pulse and the stimulus pulse are produced from the same laser pulse.

19. The method of claim 16, wherein the laser comprises a mode-locked Ti:S laser.

20. The method of claim 12, wherein at least one of a phase and a polarization of the stimulus pulse are modulated.

21. The method of claim 12, wherein at least one of a phase and a polarization of at least one of the first or second probe pulse are modulated.

22. The method of claim 12, wherein the molecular system comprises at least two different types of molecules having CARS signatures.

23. The method of claim 12, further labeling nanoparticles with Raman-active molecules to provide Raman tags which enhance the CARS response signal.

24. The method of claim 23, wherein the Raman tags bond to biological materials to be probed.

25. The method of claim 12 wherein the providing an analysis of the molecular system further comprises providing at least one of a measurement response of the molecular system to at least one agent, an identification of a genetic make up of cells in the molecular system, and an identification of a developmental stage of the molecular system.

* * * * *